US012575926B2

(12) United States Patent (10) Patent No.: US 12,575,926 B2
Humair (45) Date of Patent: Mar. 17, 2026

(54) PROSTHETIC VALVE LEAFLET

(71) Applicant: Boston Scientific Limited, Hamilton (BM)

(72) Inventor: Arnaud Humair, Mont-sur-Rolle (CH)

(73) Assignee: Boston Scientific Limited, Hamilton (BM)

( * ) Notice: Subject to any disclaimer, the term of this patent is extended or adjusted under 35 U.S.C. 154(b) by 1106 days.

(21) Appl. No.: 17/383,839

(22) Filed: Jul. 23, 2021

(65) Prior Publication Data

US 2021/0346157 A1 Nov. 11, 2021

Related U.S. Application Data

(63) Continuation of application No. 16/168,006, filed on Oct. 23, 2018, now Pat. No. 11,071,625.

(60) Provisional application No. 62/575,720, filed on Oct. 23, 2017.

(51) Int. Cl.
A61F 2/24 (2006.01)
(52) U.S. Cl.
CPC .......... A61F 2/2418 (2013.01); A61F 2/2412 (2013.01); A61F 2/2415 (2013.01); A61F 2230/005 (2013.01); A61F 2230/0056 (2013.01); A61F 2250/0036 (2013.01); A61F 2250/0037 (2013.01)
(58) Field of Classification Search
CPC ..... A61F 2/2412; A61F 2/2418; A61F 2/2475
See application file for complete search history.

(56) References Cited

U.S. PATENT DOCUMENTS

| 5,037,434 A | 8/1991 | Lane |
| 6,174,331 B1 | 1/2001 | Moe et al. |
| 6,916,338 B2 | 7/2005 | Speziali |
| 9,232,996 B2 | 1/2016 | Sun et al. |
| 9,504,564 B2 | 11/2016 | Nguyen et al. |
| 9,610,163 B2 | 4/2017 | Khairkhahan et al. |
| 9,662,204 B2 | 5/2017 | Hariton et al. |
| 11,071,625 B2 | 7/2021 | Humair |
| 2011/0282440 A1 | 11/2011 | Cao et al. |
| 2014/0155995 A1 | 6/2014 | Sun et al. |
| 2014/0243967 A1 | 8/2014 | Salahieh et al. |

(Continued)

FOREIGN PATENT DOCUMENTS

| CN | 103687574 | 3/2014 |
| CN | 103930069 | 7/2014 |
| CN | 107198594 | 9/2017 |

(Continued)

OTHER PUBLICATIONS

"Response to Communication Pursuant to Article 94(3) EPC," for European Patent Application No. 18796383.0 filed Mar. 8, 2024 (11 pages).

(Continued)

*Primary Examiner* — Brian A Dukert
(74) *Attorney, Agent, or Firm* — Pauly, DeVries Smith & Deffner LLC

(57) ABSTRACT

Embodiments include a valve leaflet for an implantable valve device comprising a leaflet body. The leaflet body comprising a free edge configured for coaptation with free edges of one or more other valve leaflets; and a root edge disposed opposite the free edge. The free edge defining an (Continued)

edge profile comprising a peak and valleys disposed on opposite sides of the peak. Other embodiments are also included herein.

17 Claims, 19 Drawing Sheets

(56)                    References Cited

U.S. PATENT DOCUMENTS

| | | |
|---|---|---|
| 2016/0067038 A1 | 3/2016 | Park et al. |
| 2019/0117391 A1 | 4/2019 | Humair |

FOREIGN PATENT DOCUMENTS

| | | |
|---|---|---|
| CN | 111278387 | 6/2020 |
| EP | 2677965 | 1/2014 |
| EP | 3697345 | 8/2020 |
| GB | 2513194 | 10/2014 |
| JP | 2003504152 | 2/2003 |
| JP | 2021500155 | 1/2021 |
| WO | 2012161786 | 11/2012 |
| WO | 2017013578 | 1/2017 |
| WO | 2019081453 | 5/2019 |

OTHER PUBLICATIONS

"Communication Pursuant to Article 94(3) EPC," for European Patent Application No. 18796383.0 filed Dec. 6, 2023 (5 pages).

File History for U.S. Appl. No. 16/168,006 downloaded Sep. 29, 2021 (259 pages).

"First Office Action," for Chinese Patent Application No. 201880064612.3 mailed Jul. 6, 2021 (13 pages) with English Summary.

"International Preliminary Report on Patentability," for PCT Application No. PCT/EP2018/078945 mailed May 7, 2020 (7 pages).

"International Search Report and Written Opinion," for PCT Application No. PCT/EP2018/078945 mailed Feb. 1, 2019 (13 pages).

"Office Action," for Japanese Patent Application No. 2020-522876 mailed May 18, 2021 (8 pages) with English Translation.

"Response to Communication Pursuant to Rules 161(1) and 162 EPC," for European Patent Application No. 18796383.0 filed Dec. 11, 2020 (10 pages).

"Second Office Action," for Chinese Patent Application No. 201880064612.3 mailed Mar. 17, 2022 (8 pages) with English Summary.

PROSTHETIC VALVE LEAFLET

This application is a continuation of U.S. patent application Ser. No. 16/168,006, filed Oct. 23, 2018, which claims the benefit of U.S. Provisional Application No. 62/575,720, filed Oct. 23, 2017, the content of which is herein incorporated by reference in its entirety.

FIELD

Embodiments herein relate to prosthetic valves, valve leaflets and related methods.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, the blood within a heart chamber can regurgitate, or leak backwards through the valve.

Valve regurgitation may be treated by replacing or repairing a diseased valve, such as an aortic valve. Surgical valve replacement is one method for treating the diseased valve. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues.

SUMMARY

Aspects herein relate to prosthetic valves, valve leaflets and related methods. In a first aspect, a valve leaflet for an implantable valve device is included having a leaflet body. The leaflet body can include a free edge configured for coaptation with free edges of one or more other valve leaflets and a root edge disposed opposite the free edge. The free edge can define an edge profile including a peak and valleys disposed on opposite sides of the peak.

In a second aspect, in addition to one or more of the preceding or following aspects, or in the alternative to some aspects, the thickness of the leaflet body can be greater at the peak than at the valleys.

In a third aspect, in addition to one or more of the preceding or following aspects, or in the alternative to some aspects, the thickness of the leaflet body at the peak is from 0.3 to 0.4 mm and at the valleys is from 0.2 to 0.3 mm.

In a fourth aspect, in addition to one or more of the preceding or following aspects, or in the alternative to some aspects, the distance between the peak and the valleys along an axis extending from the free edge to the root edge is approximately 0.5 mm to 4 mm.

In a fifth aspect, in addition to one or more of the preceding or following aspects, or in the alternative to some aspects, the distance between the peak and the valleys along an axis extending from the free edge to the root edge is approximately 1 mm to 3 mm.

In a sixth aspect, in addition to one or more of the preceding or following aspects, or in the alternative to some aspects, the distance between the peak and the valleys along an axis extending from the free edge to the root edge is approximately 5 to 20 percent of the overall height of the leaflet body along the same axis.

In a seventh aspect, in addition to one or more of the preceding or following aspects, or in the alternative to some aspects, the distance between the peak and the valleys along an axis extending from the free edge to the root edge is approximately 10 to 15 percent of the overall height of the leaflet body along the same axis.

In an eighth aspect, in addition to one or more of the preceding or following aspects, or in the alternative to some aspects, the distance between the peak and each adjoining valley along an axis perpendicular to the axis extending from the free edge to the root edge is from 4 mm to 9 mm.

In a ninth aspect, in addition to one or more of the preceding or following aspects, or in the alternative to some aspects, the width of the peak at ½ height is from 10 to 20 percent of the overall width of the leaflet body excluding any commissural mounting tabs.

In a tenth aspect, in addition to one or more of the preceding or following aspects, or in the alternative to some aspects, the width of the leaflet body excluding any commissural mounting tabs is from 20 to 30 mm.

In an eleventh aspect, in addition to one or more of the preceding or following aspects, or in the alternative to some aspects, the leaflet body can further include commissural mounting tabs disposed on opposed lateral sides of the leaflet body.

In a twelfth aspect, in addition to one or more of the preceding or following aspects, or in the alternative to some aspects, the peak can be interrupted by a notch.

In a thirteenth aspect, in addition to one or more of the preceding or following aspects, or in the alternative to some aspects, the peak can be centered along a width of the leaflet body.

In a fourteenth aspect, a valve leaflet for an implantable valve device is included having a leaflet body including a coaptation edge configured for coaptation with coaptation edges of one or more other valve leaflets. The coaptation edge can define an edge profile comprising a convex portion, wherein the convex portion has a width that is less than a width of the coaptation edge. A width of the convex portion at ½ height relative to the rest of the coaptation edge is less than half of a width of the leaflet body.

In a fifteenth aspect, in addition to one or more of the preceding or following aspects, or in the alternative to some aspects, wherein the edge profile further comprises a first concave portion disposed on a first lateral side of the convex portion and a second concave portion disposed on a second lateral side of the convex portion.

In a sixteenth aspect, in addition to one or more of the preceding or following aspects, or in the alternative to some aspects, a third concave portion can be included that is disposed within the convex portion such that the convex portion comprises a first convex portion and a second convex portion.

In a seventeenth aspect, in addition to one or more of the preceding or following aspects, or in the alternative to some aspects, the thickness of the leaflet body is greater at the convex portion than at the first concave portion and the second concave portion.

In an eighteenth aspect, in addition to one or more of the preceding or following aspects, or in the alternative to some aspects, the valve leaflet can include tissue obtained from an animal.

In a nineteenth aspect, in addition to one or more of the preceding or following aspects, or in the alternative to some aspects, an implantable valve is included having a frame and three valve leaflets attached to the frame. Each valve leaflet can include a leaflet body including a free edge configured for coaptation with free edges of one or more other valve leaflets and a root edge disposed opposite the free edge. The free edge can define an edge profile including at least two inflection points.

In a twentieth aspect, in addition to one or more of the preceding or following aspects, or in the alternative to some aspects, wherein each edge profile can include a third inflection point and a fourth inflection point.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The human body has four heart valves: a pulmonary valve, a tricuspid valve, an aortic valve and a mitral valve. The purpose of the heart valves is to allow blood to flow in a particular direction through the heart and from the heart into the major blood vessels connected to the heart, such as the aorta and pulmonary artery. Prosthetic valves designed to replace a valve in a human body frequently include two or more leaflets (commonly three) that can be configured to allow one way flow through the valve, such as by separating from each other to open the valve or joining together (valve leaflet coaptation) to close the valve.

The performance of a valve can highly depend on the leaflets. Various embodiments of leaflets are disclosed herein. In some embodiments, a free edge of a leaflet has a "W"-like shape. The free edge can include a peak with a valley disposed on either side of the peak. The "W"-like shape can provide better coaptation between the leaflets resulting in a more complete seal when the valve is closed thereby reducing the risk or possibility of leakage or regurgitation. A leaflet with a "W"-like shape can also allow for easier assembly or installation of a valve. In some embodiments, the peak can be a central peak, but in other embodiments the peak can be off-center. A central peak can allow an assembler to more easily locate the center of the free edge resulting in more accurate assembly of the leaflets or prevent misalignment between leaflets leading to poor coaptation. The leaflets disclosed herein can also have greater durability compared to traditional leaflets.

A "W"-like shape can refer to the profile of a free edge of a leaflet with a central peak between two valleys. Profiles of free edges of valve leaflets herein can also include a free edge of a leaflet with at least one convex portion and two concave portions. Profiles of free edges of valve leaflets herein can also include a free edge of a leaflet with at least two inflections points. Profiles of free edges of valve leaflets herein can also include a free edge of a leaflet including at least three arcs with at least two reversals of curvature such that the central arc has a direction of curvature that is opposite that of the arcs on either side of the central arc.

Figure 1:
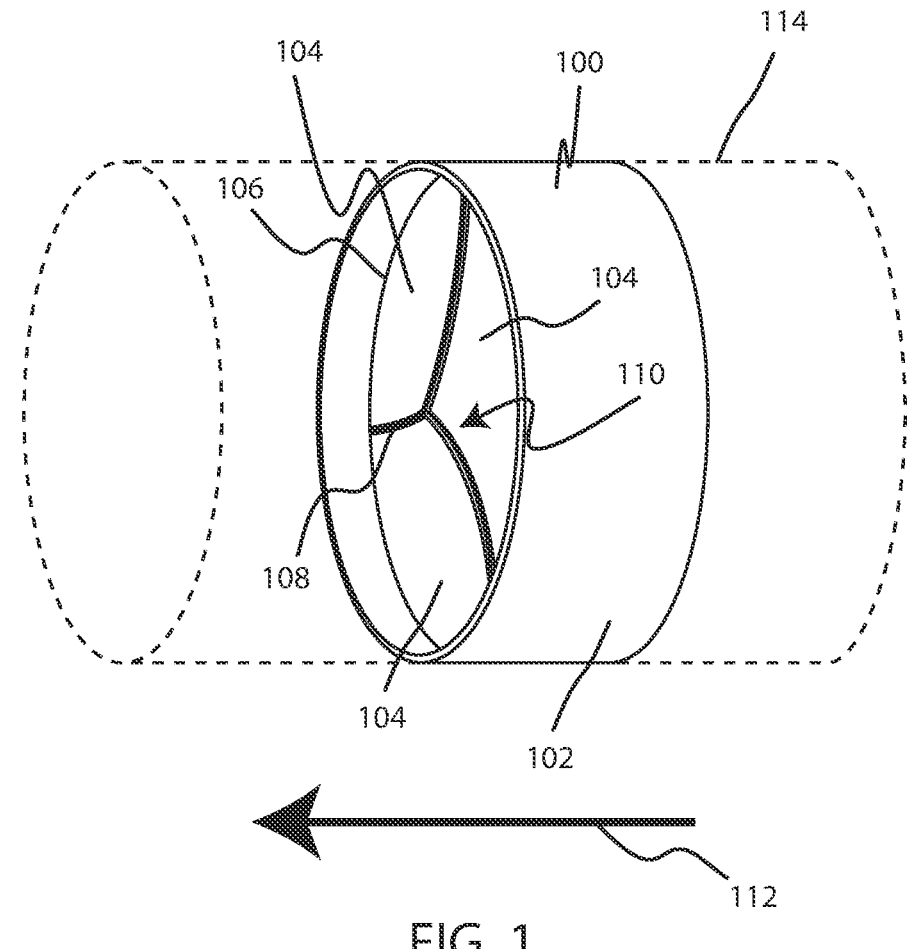
FIG. 1 is a schematic perspective view of a closed valve in a portion of an environment where it can be used, according to various embodiments.
Figure 2:
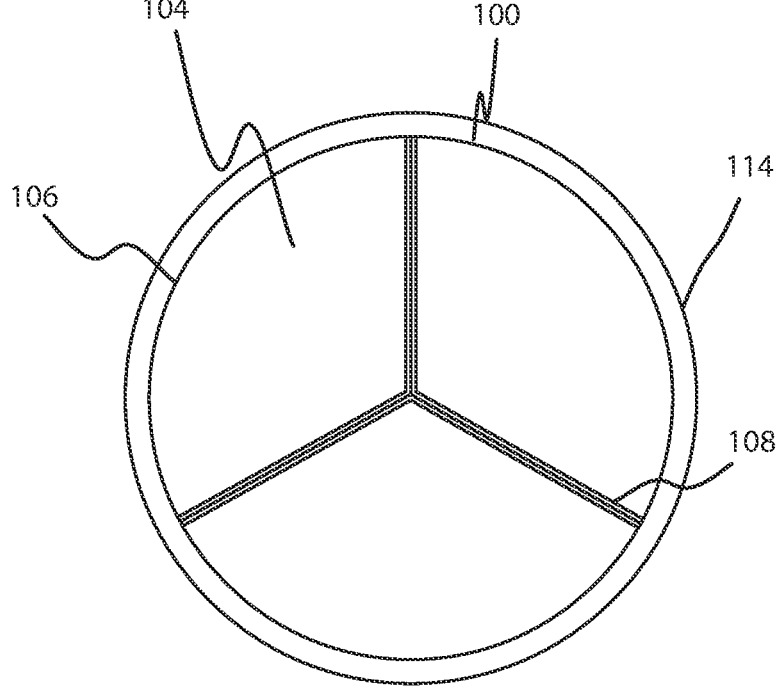
FIG. 2 is a schematic end view of a closed valve in a portion of an environment where it can be used, according to various embodiments.

FIG. 1 shows a schematic view of a closed valve 100 in a vessel 114, according to various embodiments. FIG. 2 shows an end view of the closed valve 100. The valve 100 can be configured to allow one-way flow through the valve 100, such as depicted by arrow 112.

The valve 100 can include a base 102 defining a substantially cylindrical passage and a plurality of leaflets 104 disposed along the substantially cylindrical passage. In various embodiments, the base 102 can be substantially circular. In other embodiments, the base 102 can define a non-circular shape, such as a D-shape. In some embodiments, a non-circular base 102 can be used to repair a mitral valve or another non-circular valve in the body.

Each leaflet 104 includes a respective root edge 106 coupled to the base 102 and a respective free edge 108 movable relative to the root edge 106 to coapt with the free edges 108 of the other polymeric leaflets 104 along the coaptation region 110. In some embodiments, the plurality of leaflets 104 can be integrally formed with each other, such that the leaflets are formed as a single unit from a single sheet of material. It should be appreciated that the valve 100 can be any type of heart valve (e.g., a mitral valve, an aortic valve, etc.). In some embodiments, a "root edge" can be an actual cut or otherwise formed edge of the material used to form the valve leaflets. However, in other embodiments, the valve leaflet can be formed integrally with other structures such as an integral skirt, base structures, liners, leaflets or the like and thus in those circumstances the "root edge" is not actually a cut or otherwise divided edge, but rather is the place opposite the free edge where the valve leaflet integrally meets those other structures.

In use, the valve 100 is implanted (e.g., surgically or through transcatheter delivery) in a mammalian heart. The free edges 108 of the leaflets 104 move into coaptation with one another in a closed position (FIGS. 1 and 2) to substantially restrict fluid from flowing past the valve 100 in a closed position. The leaflets 104 can coapt to fill up or close the central aperture of the valve 100 thereby impeding the flow of fluid opposite to arrow 112.

Figure 3:
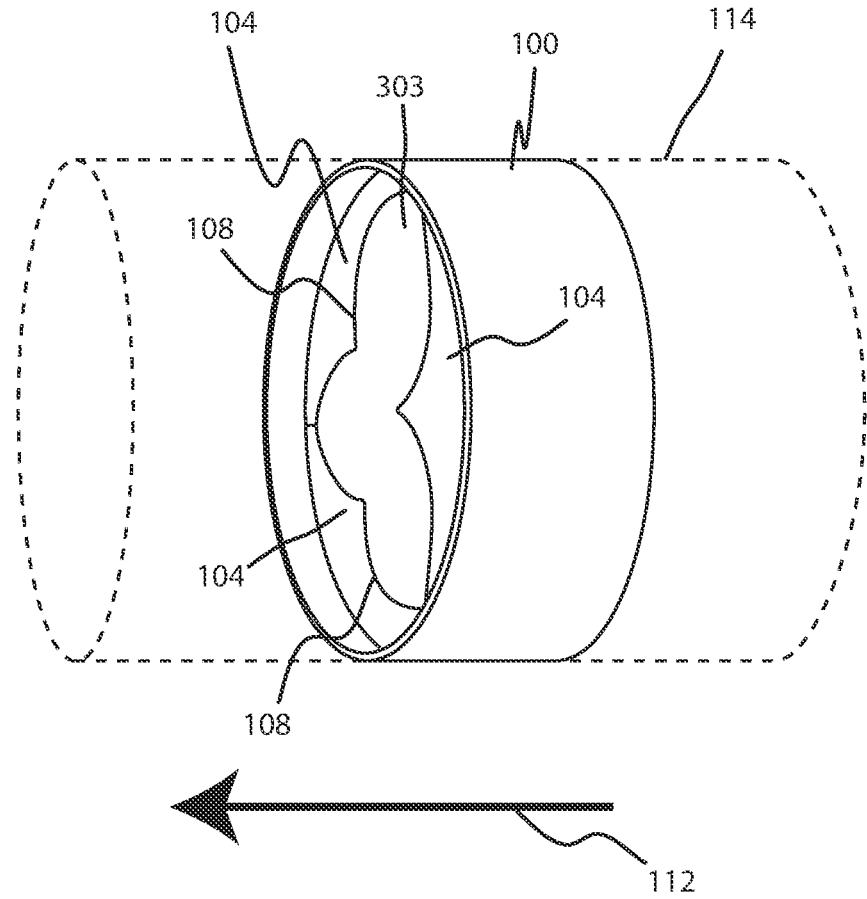
FIG. 3 is a schematic perspective view of an open valve in a portion of an environment where it can be used, according to various embodiments.
Figure 4:
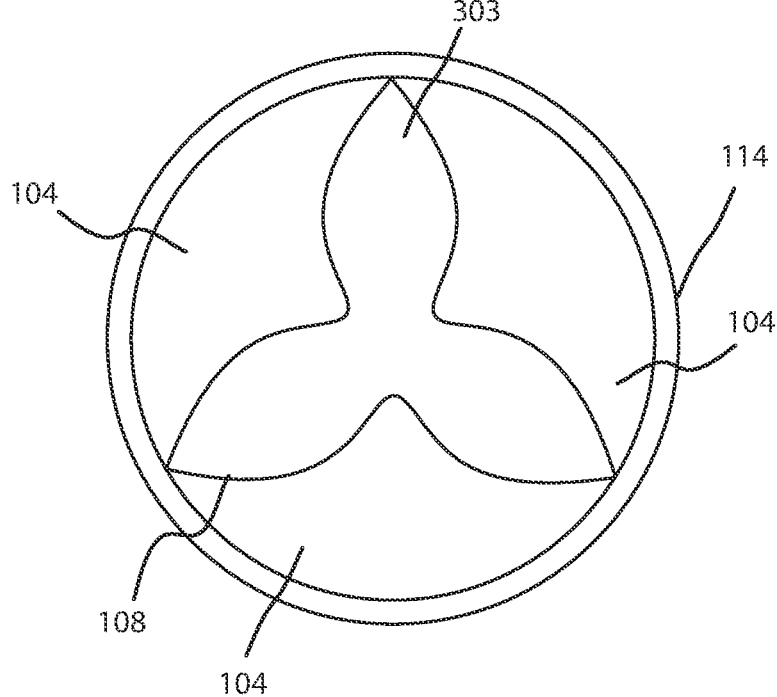
FIG. 4 is a schematic end view of an open valve in a portion of an environment where it can be used, according to various embodiments.

FIGS. 3 and 4 show a schematic view of an open valve 100 in the vessel 114. FIG. 3 shows a perspective view and FIG. 4 shows an end view of the valve 100 in the vessel 114. The free edges 108 of the leaflets 104 move away from one another to an open position (FIGS. 3 and 4) permitting fluid to flow past the valve 100 through aperture 303 in the direction of arrow 112. Movement of the leaflets 104 between the closed and open positions can substantially approximate the hemodynamic performance of a healthy, natural valve. Flow of fluid, such as blood, in the direction of arrow 112 can apply a pressure on the leaflets 104 which can result in the leaflets 104 separating from each other to define the aperture 303 which can allow the fluid to flow through the valve 100.

Figure 5:
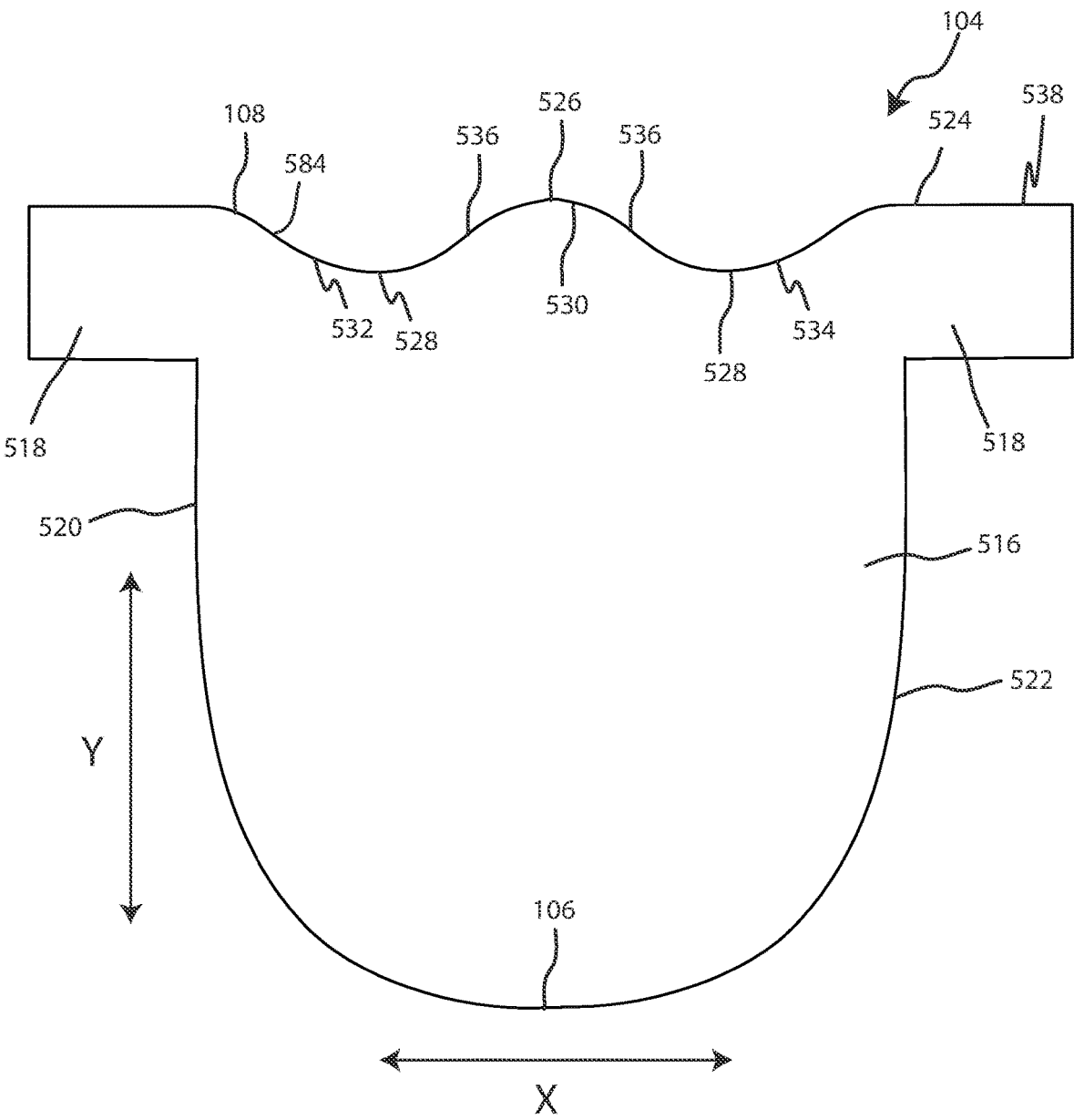
FIG. 5 is a schematic front view of a prosthetic valve leaflet, according to various embodiments.

FIG. 5 shows a front view of a leaflet 104, according to various embodiments. As shown, leaflet 104 can include a body portion 516 (or belly region of the leaflet) and two commissural mounting tabs 518. The mounting tabs 518 can be disposed on opposed lateral sides of the leaflet body 516. The mounting tabs 518 can extend outwardly from the body portion 516 and can be used to attach the leaflets to a frame.

In some embodiments, the body portion 516 has a bottom or root edge 106, a first side edge 520, a second side edge 522, and a free edge 108. Leaflet 104 further includes a front side (i.e., the side that blood flows toward or upstream side), a back side (i.e., the side that blood flows away from or downstream side). The root edge 106 and side edges 520, 522 of the body portion 516 can be shaped for suturing and for forming a leaflet profile similar to a native valve. In various embodiments, the root edge 106 can be integral with other tissues, such as an integral skirt or other leaflets, such that the root edge 106 is not a standalone edge. The mounting tabs 518 can be shaped to be compatible with anchor elements, such as anchor elements shown in FIG. 12.

The free edge 108 can define an edge profile 524 comprising a central peak 526 and valleys 528 disposed on opposite sides of the central peak 526. The free edge 108 can include a coaptation edge 584 and a top edge 538 of the mounting tabs 518. The coaptation edge 584 is the portion of the free edge 108 that is configured for coaptation with the coaptation edge of at least one adjacent leaflet included in the valve 100. In some embodiments, the coaptation edge 584 can extend from the top edge 538 of one of the mounting tabs 518 to the top edge 538 of the other mounting tab 518.

The central peak 526 can be central such that the apex of the central peak 526 is located between the mounting tabs 518, between the first side edge 520 and the second side edge 522, or between the right side limit of the leaflet body 516 and the left side limit of the leaflet body 516. In some embodiments, the central peak 526 can be centered between the mounting tabs 518, such that the apex of the central peak 526 is located an equal distance from each of the mounting tabs 518. In some embodiments, the central peak 526 can be central such that the apex of the central peak 526 is located within a region defined by the central 10% of the overall width of the leaflet between the mounting tabs 518. In some embodiments, the leaflet 104 can have an axis of symmetry that extends through the apex of the central peak 526 and that is parallel to the Y axis (e.g., perpendicular to an axis that is tangent to the apex of the central peak 526 or the X axis). The central peak 526 can include a local maximum, such that the distance from adjacent portions of free edge 108 to the root edge 106 is less than the distance from the apex of the central peak 526 to the root edge 106. Each of the valleys 528 can include a local minimum, such that the distance from adjacent portions of the free edge 108 to the root edge 106 is greater than the distance from the valleys 528 to the root edge 106.

Figure 6:
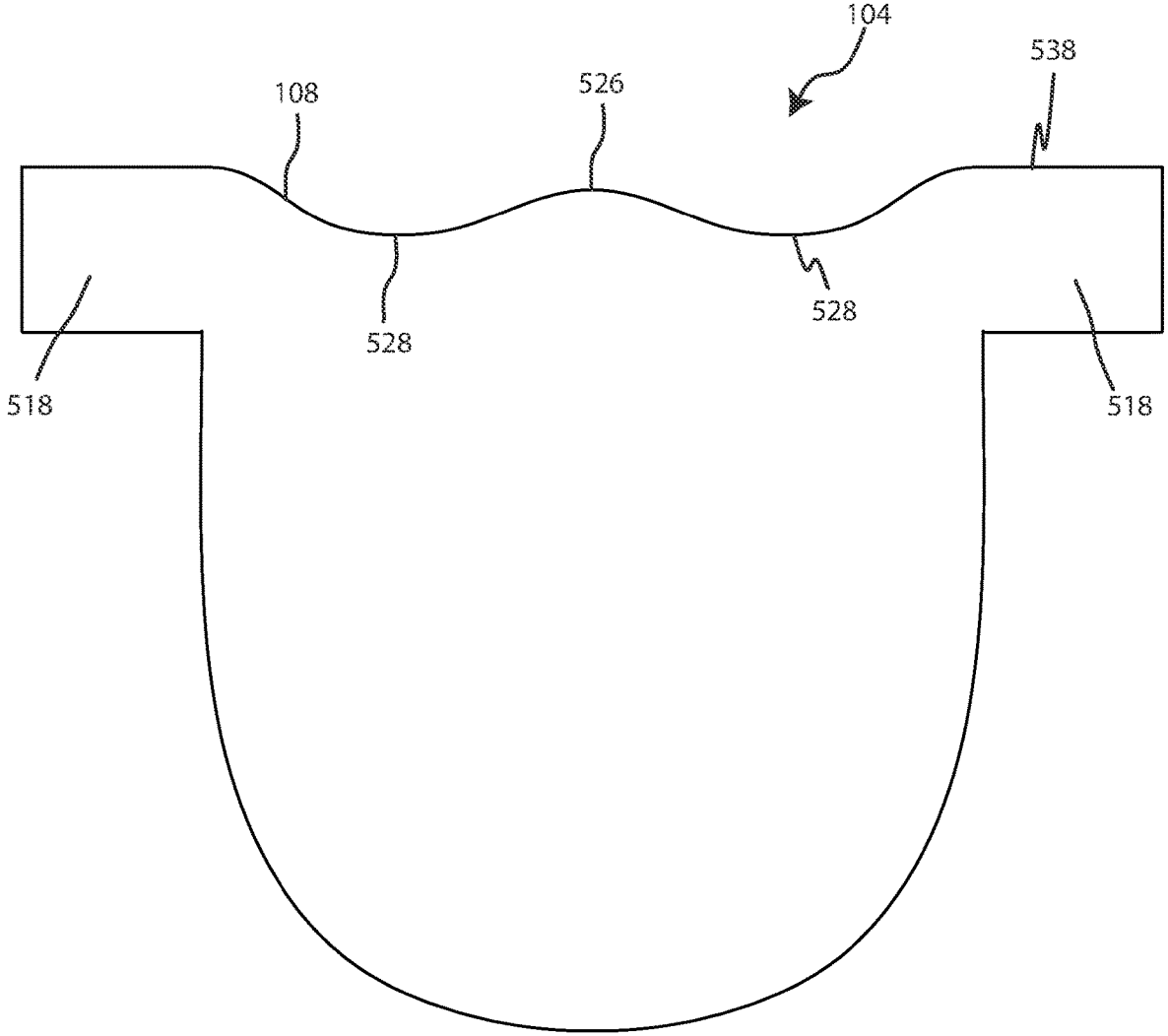
FIG. 6 is a schematic front view of a prosthetic valve leaflet, according to various embodiments.
Figure 7:
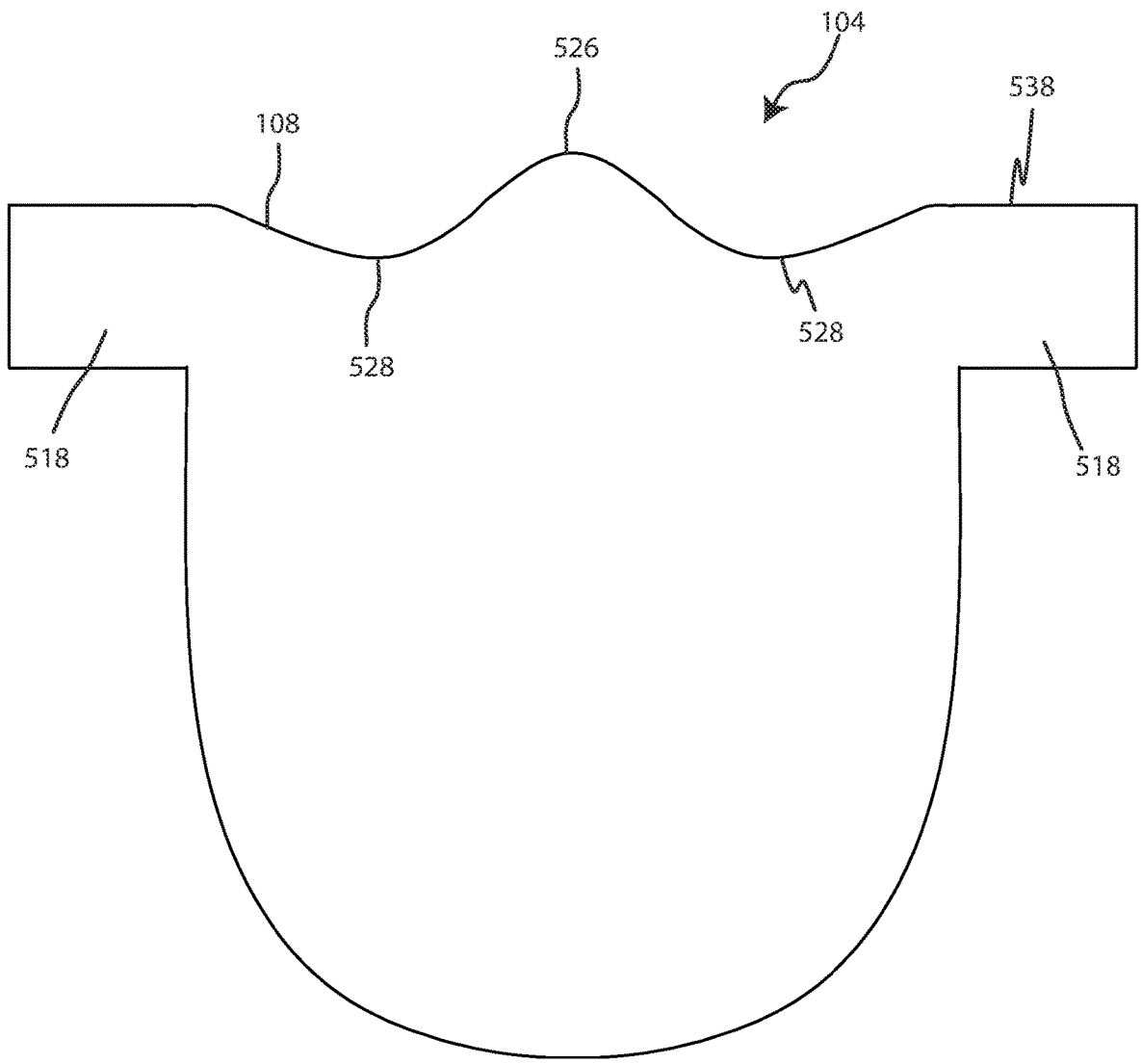
FIG. 7 is a schematic front view of a prosthetic valve leaflet, according to various embodiments.

In various embodiments, the central peak 526 can be substantially equal to the top edge 538 of the mounting tabs 518, such as shown in FIG. 5. In other embodiments, the apex of the central peak 526 can be located below the top edge 538 of the mounting tabs 518 or closer to the root edge 106, such as shown in FIG. 6. In other embodiments, the apex of the central peak 526 can extend past the top edge 538 of the mounting tabs 518 or further away from the root edge 106, such as shown in FIG. 7.

In various embodiments, free edge 108 can include a convex portion 530, a first concave portion 532, and a second concave portion 534. The convex portion 530 can include the central peak 526. The first concave portion 532 and the second concave portion 534 can each include a valley 528. The first concave portion 532 can be disposed on a first lateral side of the convex portion 530 and the second concave portion 534 can be disposed on a second lateral side of the convex portion 530, such that the first concave portion 532 can be disposed on the opposite side of the convex portion 530 from the second concave portion 534.

The free edge 108 can include one or more inflection points 536. In some embodiments, the free edge 108 includes two inflection points 536, such as one inflection point 536 on either side of the central peak 526. In various embodiments, the free edge 108 can include three inflection points 536. In various embodiments, the free edge 108 can include four inflection points 536, such as one on either side of each of the valleys 528. In various embodiments, the free edge 108 can include five inflection points 536. In various embodiments, the free edge 108 can include six inflection points 536. An inflection point 536 can refer to a point or portion of the free edge 108 where the free edge 108 transitions from concave to convex, such as where the second derivative of a function describing the free edge 108 profile is equal to zero.

In some embodiments, the free edge 108 can have a profile including a free edge of a leaflet including at least three arcs with at least two reversals of curvature such that the central arc has a direction of curvature that is opposite that of the arcs on either side of the central arc. For example, valleys 528 can be formed by two arcs and central peak 526 can be formed by a third arc, between the first two arcs. The third arc can have a direction of curvature that is opposite from the first two arcs. As such, the profile can include two reversals of curvature with the first between the first valley 528 and the central peak 526 and the second between the central peak and the second valley 528. The radii of curvature of the arcs can vary. In some embodiments, the arc forming the central peak can have a smaller radius of curvature than the other arcs forming the valleys. However, in other embodiments, the arc forming the central peak can have a larger radius of curvature than the other arcs forming the valleys.

The height of the central peak may be equal to, less than, or greater than the height of the tops of the mounting tabs. For example, whereas FIG. 5 shows an embodiment wherein the height of the central peak is equal to the height of the tops of the mounting tabs, FIG. 6 shows a front view of a valve leaflet 104, according to various embodiments, wherein the height of the central peak is less than the height of the tops of the mounting tabs. The valve leaflet 104 can include two valleys 528 separated by a central peak 526. The leaflet can include two mounting tabs 518.

In some embodiments, the apex of the central peak 526 can be below the top edge 538 of the mounting tabs 518. The free edge 108 can extend initially from a mounting tab 518 downwards towards the root edge 106 (e.g., slopes downward moving away from the mounting tabs). Then, the central peak 526 extends upward away from the root edge 106. In various embodiments, such as shown in FIG. 6, the apex of the central peak 526 is located between the root edge 106 and the top edge 538 of the mounting tabs 518, such that the apex of the central peak 526 terminates below the top edge 538 of the mounting tabs 518.

Similar to the embodiment depicted in FIG. 5, the leaflet 104 can include two or more inflection points, three or more inflection points, or four or more inflection points. The leaflet 104 can include a first concave portion on one side of a convex portion, and a second concave portion on the other side of the convex portion.

FIG. 7 shows a front view of a valve leaflet 104, according to various embodiments, wherein the height of the central peak is greater than the height of the tops of the mounting tabs. The valve leaflet 104 can include two valleys 528 separated by a central peak 526. The leaflet can include two mounting tabs 518.

In some embodiments, the apex of the central peak 526 can extend past the top edge 538 of the mounting tabs 518. The free edge 108 can generally extend from a mounting tab 518 inwards towards the root edge 106. The central peak 526 extends away from the root edge 106 towards the top edge of the mounting tabs 518. The apex of the central peak 526 can be located past the top edge 538 of the mounting tabs 518, such that the top edge 538 of the mounting tabs 518 is located between the apex of the central peak 526 and the root edge 106.

Similar to the embodiment depicted in FIG. 5, the leaflet 104 can include two or more inflection points, three or more inflection points, or four or more inflection points. The leaflet 104 can include a first concave portion on one side of a convex portion, and a second concave portion on the other side of the convex portion.

Figure 8:
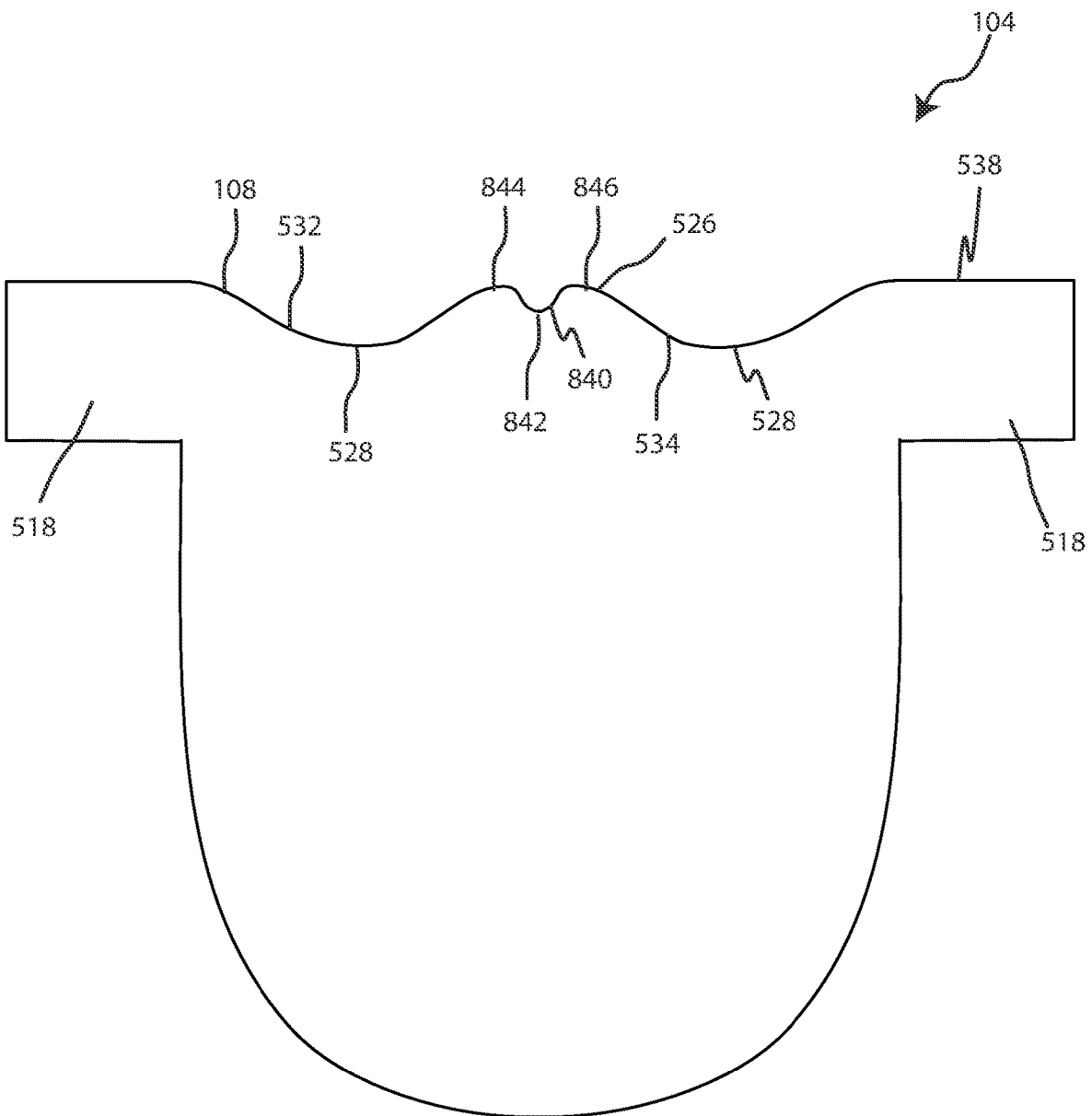
FIG. 8 is a schematic front view of a prosthetic valve leaflet, according to various embodiments.

FIG. 8 shows a front view of a valve leaflet 104, according to various embodiments. The valve leaflet 104 can include two valleys 528 separated by a central peak 526. The leaflet 104 can include two mounting tabs 518.

In various embodiments, the central peak 526 can be interrupted by a notch 840. The notch 840 can be located in the middle of the central peak 526, such as equal distance between the two mounting tabs 518. In some embodiments, the leaflet 104 can be symmetric, such as having an axis of symmetry that extends through the bottom of the notch 840.

The notch 840 can be concave. In some embodiments, the leaflet 104 can include three concave portions and two convex portions. The three concave portions can include a first concave portion 532, a second concave portion 534, and a third concave portion 842. The two convex portions can include a first convex portion 844 and a second convex portion 846. The two convex portions 844, 846 can form the central peak 526. The two convex portions 844, 846 can be located on opposite sides of the third concave portion 842. The leaflet 104 can include two or more inflection points, three or more inflection points, four or more inflection points, five or more inflection points, or six or more inflection points.

In some embodiments, the leaflet 104 can include two valleys 528 and a notch 840 (or minor valley). The bottom of the notch 840 can be a local minimum. The bottom of the valleys 528 can be local minimums as well as global minimums of the free edge 108.

The notch 840 can be non-planar, such that it is curved or rounded. The notch 840 can define a portion of a circle or ellipse. In other embodiments, the notch 840 can include planar segments, such as forming a "V"-shaped notch or recess.

Figure 9:
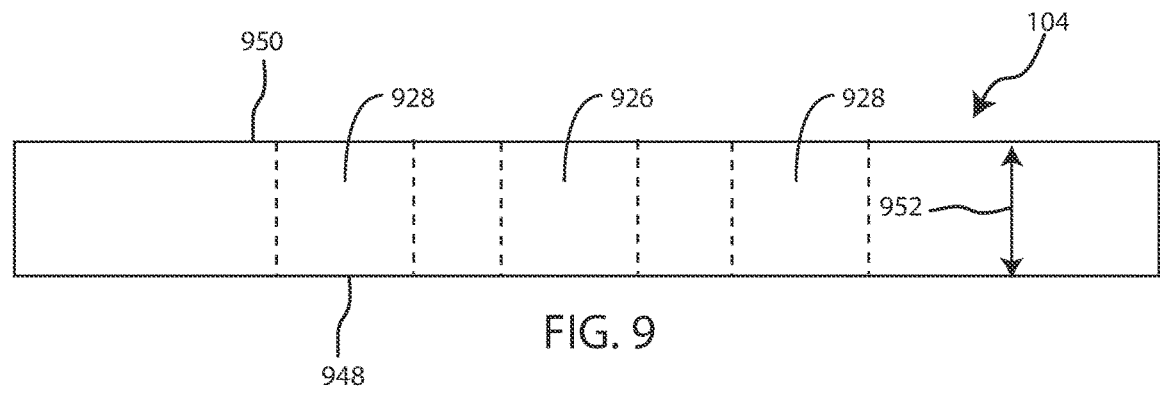
FIG. 9 is a schematic top view of a prosthetic valve leaflet, according to various embodiments.

FIG. 9 shows a top view of a valve leaflet 104, according to various embodiments. In various embodiments, the valve leaflet 104 can be planar, such that the front side 948 is substantially parallel with the back side 950. The front side 948 and the back side 950 can each be substantially planar or flat. The leaflet 104 can have a consistent thickness, such that the front side 948 maintains an equal distance from the back side 950. In some embodiments, the leaflet 104 can have a thickness 952 of at least 0.2 mm and not more than 0.4 mm. It should be understood that the top view shown in FIG. 9 can represent the top view of any of the embodiments shown in FIGS. 5-8.

Figure 10:
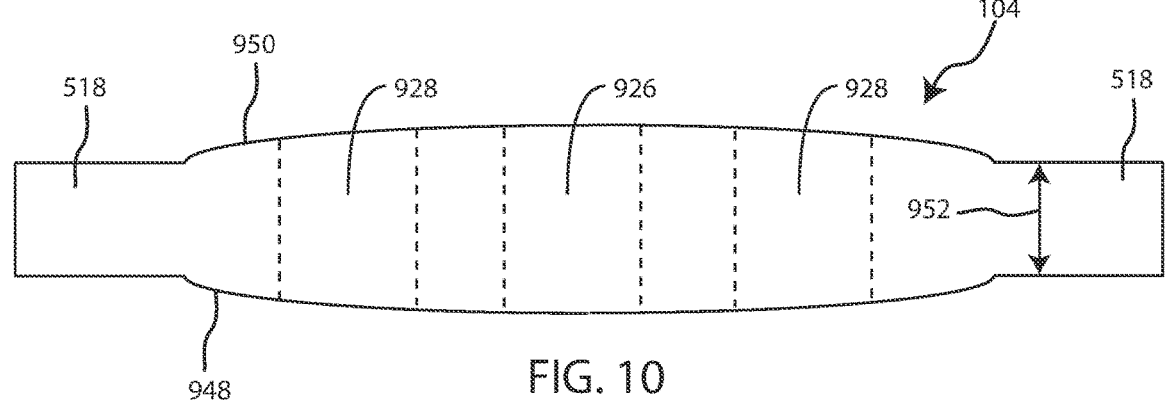
FIG. 10 is a schematic top view of a prosthetic valve leaflet, according to various embodiments.

FIG. 10 shows a top view of a valve leaflet 104, according to various embodiments. In various embodiments, the valve leaflet 104 can be non-planar, such that the front side 948 and/or back side 950 are non-planar or non-flat. The front side 948 can be non-parallel with the back side 950. In some embodiments, the valve leaflet 104 can include an axis of symmetry, such that the back side 950 can be a mirror image of the front side 948 when viewed from the top, such as shown in FIG. 10. However, in other embodiments, the valve leaflet 104 can exhibit an asymmetry between the front side 948 and the back side 950.

In various embodiments, the valve leaflet 104 can increase in thickness as it approaches the middle of the leaflet 104, such that the middle of the leaflet 104 can be the thickest portion of the leaflet 104. In some embodiments, the mounting tabs 518 can be planar and the leaflet body 516 can be non-planar. In some embodiments, the leaflet body 516 can continually increase in thickness towards the middle, such that a portion of the body 516 that is closer to the middle will be thicker than a portion that is further from the middle. In some embodiments, the central peak 526 can have a greater thickness than the valleys 528. In some embodiments, the central peak 526 has the greatest thickness of any portion of the leaflet 104. In some embodiments, the thickness of the leaflet body 516 at the central peak 526 can be at least 0.3 mm and not more than 0.4 mm, and the thickness at the valleys 528 can be at least 0.2 mm and not more than 0.3 mm.

It should be understood that the top view shown in FIG. 10 can represent the top view of any of the embodiments shown in FIGS. 5-8.

Figure 11:
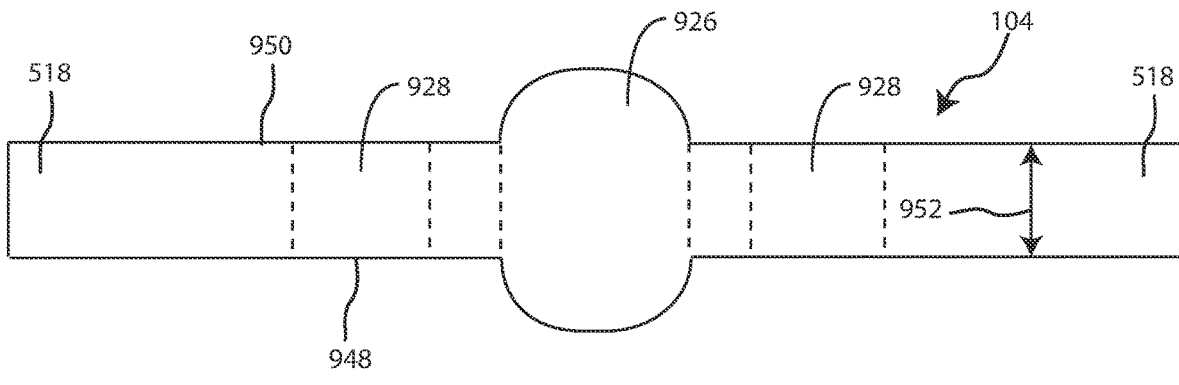
FIG. 11 is a schematic top view of a prosthetic valve leaflet, according to various embodiments.

As yet another example, FIG. 11 shows a top view of a prosthetic valve leaflet 104, according to various embodiments. In various embodiments, the front side 948 can be planar and parallel with the back side 950 along at least a portion of the width of the leaflet body 516. In various embodiments, the front side 948 can be parallel with the back side 950 along the mounting tabs 518 and along the valleys 528. In some embodiments, the front side 948 can be parallel with the back side 950 along all portions of the leaflet body 516 with the exception of the central peak 526. In various embodiments, the front side 948 can be non-parallel with the back side 950 in between two inflection points that are on opposite side of the central peak 526, such that the front side 948 and back side 950 are not parallel along the central peak 526. The thickness of leaflet body 516 can be greater at the central peak 526 than at the valleys 528.

In various embodiments, the thickness 952 of the leaflet body 516 at the central peak 526 can be at least 0.3 mm and not more than 0.4 mm. In various embodiments, the thickness 952 of the leaflet body 516 at the valleys 528 can be at least 0.2 mm and not more than 0.3 mm.

It should be understood that the top view shown in FIG. 11 can represent the top view of any of the embodiments shown in FIGS. 5-8.

Figure 12:
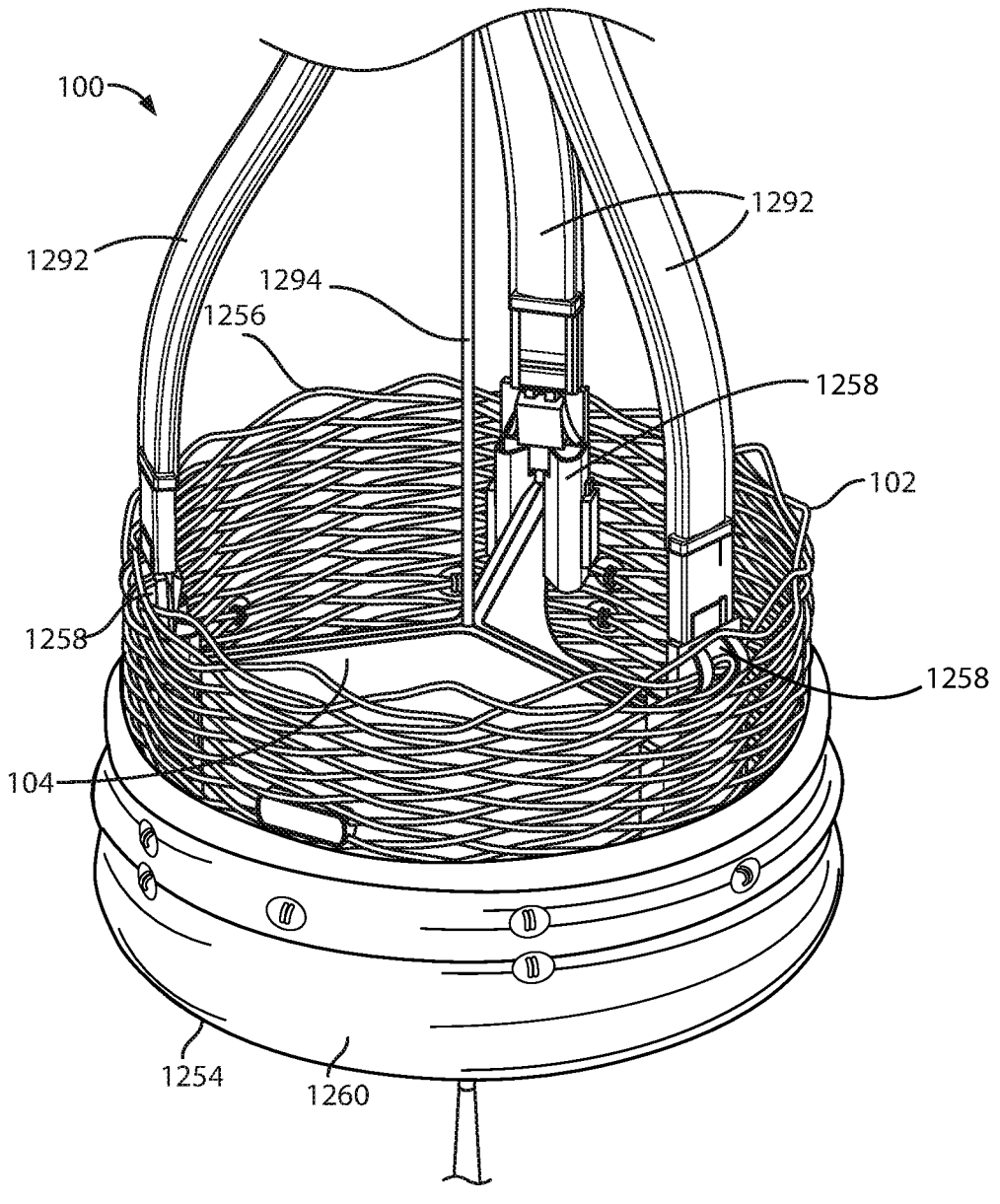
FIG. 12 is a schematic perspective view of a prosthetic valve leaflet in a frame, according to various embodiments.

FIG. 12 shows a perspective view of a valve 100, according to various embodiments. The valve 100 can include an inflow end 1254 and an outlet end 1256. The valve 100 can have a substantially tubular base 102, a plurality of leaflets 104, anchor elements 1258 and a tubular seal 1260. The tubular base 102 can be a radially expandable member, e.g., annular frame or stent, having an annular cavity. As shown in FIG. 12, the valve 100 can have three heart valve leaflets 104 coupled to the tubular base 102 within the annular cavity. Three anchor elements 1258 positioned within the annular cavity of the tubular base 102 can each secure the heart valve leaflets 104 to the tubular base 102. Each anchor elements 1258 can be coupled to the tubular base 102 with an anchoring element and coupled to the leaflets 104 with a clamping element. The tubular seal 1260 can be disposed about at least a portion of the tubular base 102. In particular, the tubular seal 1260 can have a portion secured to bottom edges of the plurality of leaflets and have a portion disposed about an outer surface of the tubular base 102 to restrict blood flow around the leaflets.

FIG. 12 also shows pieces of placement hardware 1292, 1294 that are used to position and deploy the valve 100 within a subject.

Figure 13:
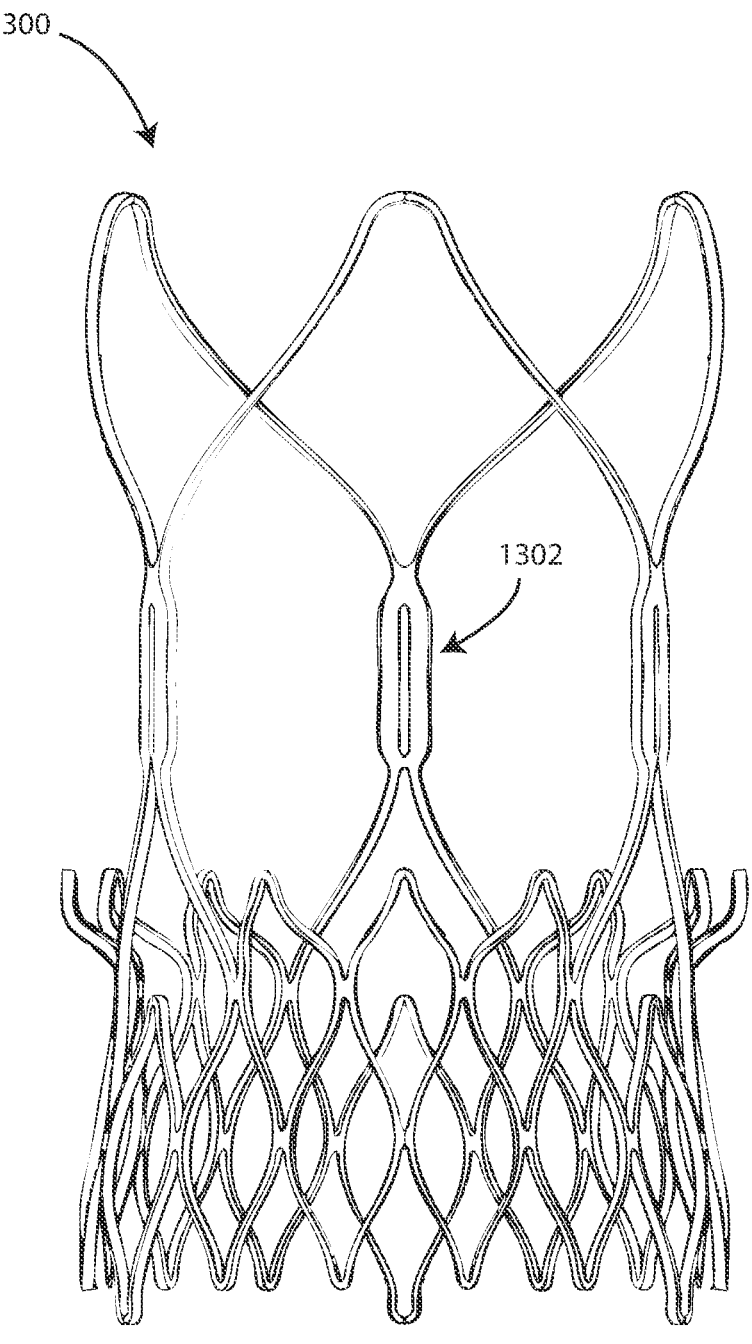
FIG. 13 is a schematic perspective view of a prosthetic valve leaflet in a frame, according to various embodiments.

It will be appreciated that while FIG. 12 shows one specific example of a valve including a particular type of valve frame, many different specific structures for valves and valve frames can be used with valve leaflets described herein. Referring now to FIG. 13, an additional example of a valve frame 1300. The valve frame 1300 can have a generally tubular shape and can include mounting points 1302 to which other elements, such as mounting tabs of valve leaflets can be attached.

Figure 14:
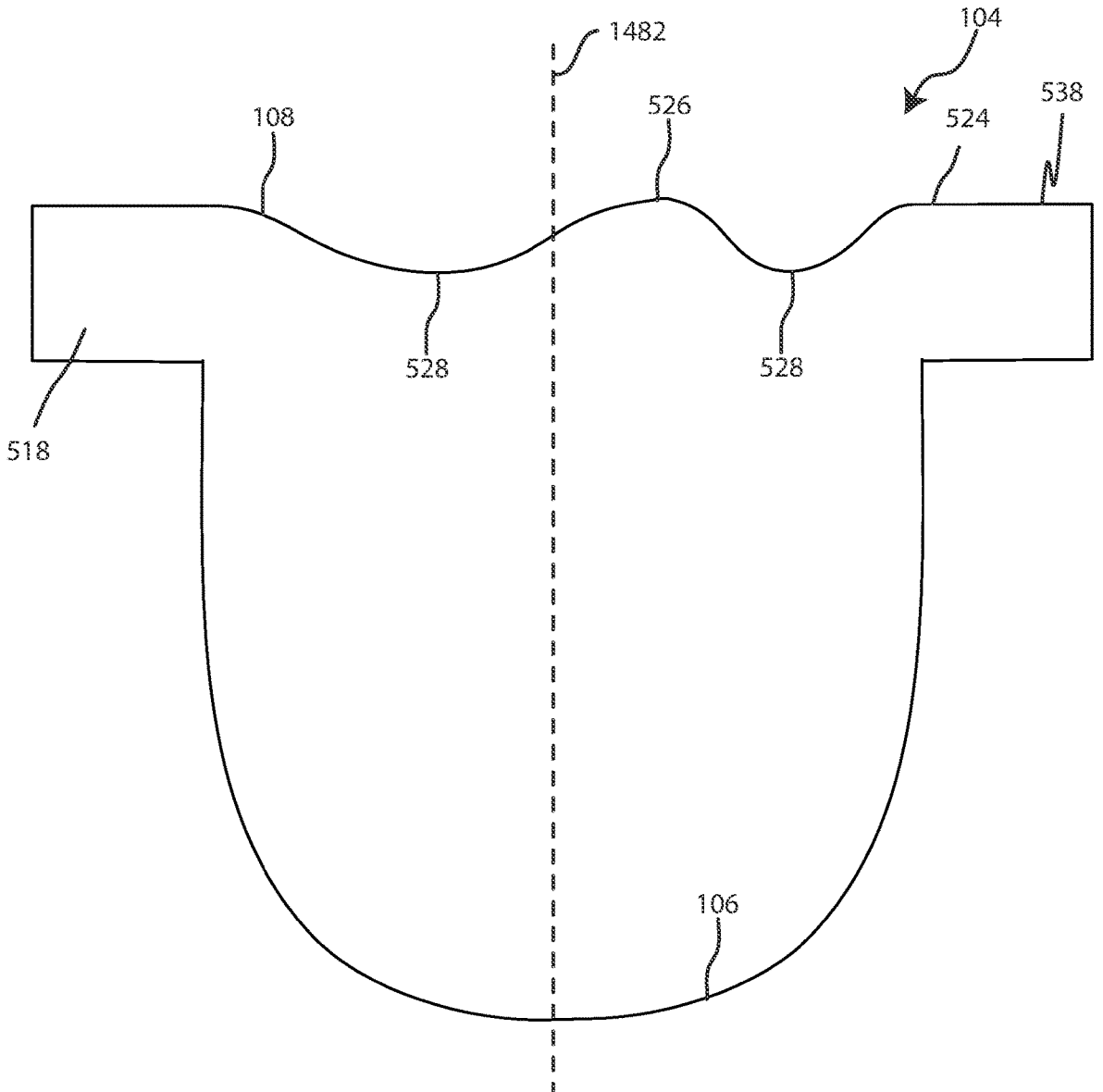
FIG. 14 is a schematic front view of a prosthetic valve leaflet, according to various embodiments.
Figure 15:
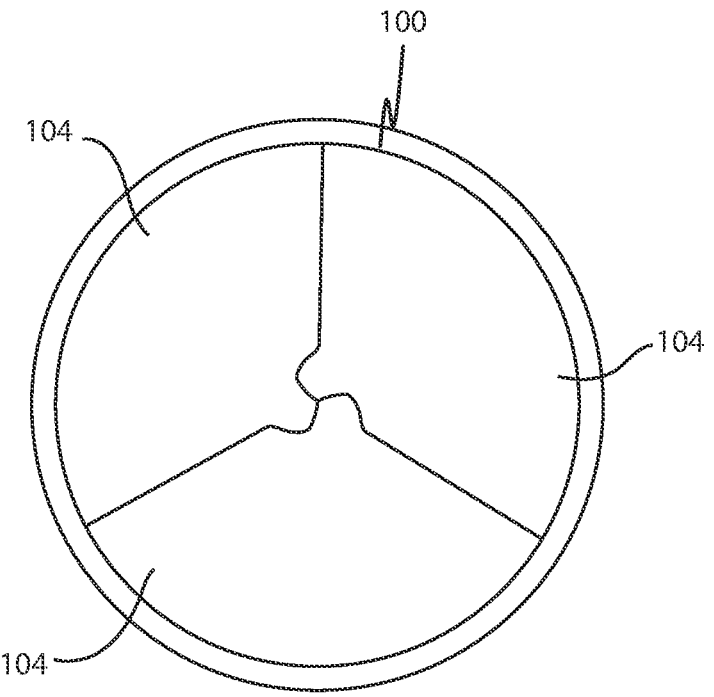
FIG. 15 is a schematic end view of a closed valve in a portion of an environment where it can be used, according to various embodiments.

In various embodiments, the leaflet 104 can be asymmetrical or include an offset central peak 526. FIG. 14 shows an embodiment of a leaflet 104 with an offset central peak 526. In some embodiments, the central peak 526 can be disposed between the mounting tabs 518 and offset from a center line 1482 which is equal distance from each mounting tab 518. In the embodiment shown in FIG. 14, the central peak 526 is offset to the right. In other embodiments, the central peak 526 can be offset to the left. FIG. 15 shows a schematic end view of a closed valve 100 with non-symmetrical leaflets 104. In some embodiments, a valve 100 can include one or more symmetrical leaflets 104, such as shown in FIGS. 5-8 and one or more non-symmetrical leaflets 104, such as shown in FIG. 14. In an embodiment, a valve 100 includes at least one symmetrical leaflet 104 and one non-symmetrical leaflet 104.

Figure 16:
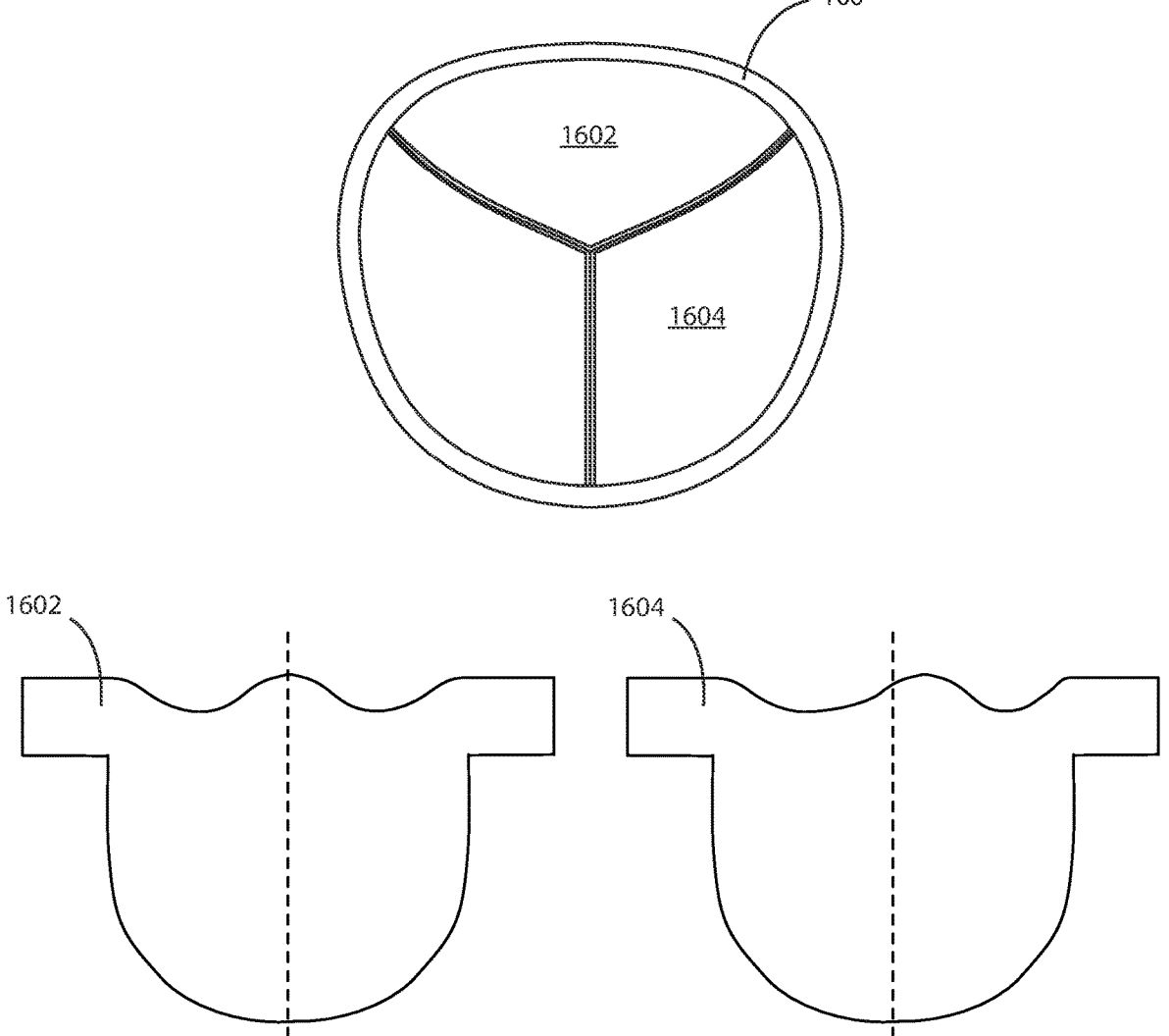
FIG. 16 is a schematic end view of a close valve with a non-circular frame and a separate view of two valve leaflets disposed therein according to various embodiments herein.

In various embodiments, the valve may not be perfectly circular when viewed from one end or another. For example, in some embodiments, the valve can be generally circular, but include one or more flat segments. In some embodiments, the valve can have a "D" shape when viewed from an end. In some embodiments, the valve can take on the shape of an oval. Referring now to FIG. 16, a schematic end view of a closed valve 100 with a non-circular frame is shown along with a view of two valve leaflets that would be disposed within the valve frame according to various embodiments herein. In this example, the frame takes on a "D" shape. Some of the valve leaflets can have a peak that is laterally equidistant from the sides of the valve leaflet (e.g., a centered peak), while other of the valve leaflets can have a peak that is laterally offset to one side or the other. In the example illustrated by FIG. 16, a first valve leaflet 1602 can have a centered peak, while a second valve leaflet 1604 can have a peak that is offset to one side (wherein the lateral center of each valve leaflet is indicated by the dashed line). The offset can vary. In some embodiments the offset (as measured from the highest point of the peak) can be 0.5, 1, 2, 3, 4, 5, 6, 7, 8, 9, 10, 12, 13, 14, 15, 16, 17, 18, 19, or 20 mm to the right or left. In some embodiments, the distance of the offset can fall within a range wherein the upper and lower bound of the range can be any of the preceding distances provided that the upper bound is greater than the lower bound. The valve 100 can also include a third leaflet with an offset peak, but with the offset being opposite that of leaflet 1604 (e.g., left offset versus right offset or vice versa).

Figure 17:
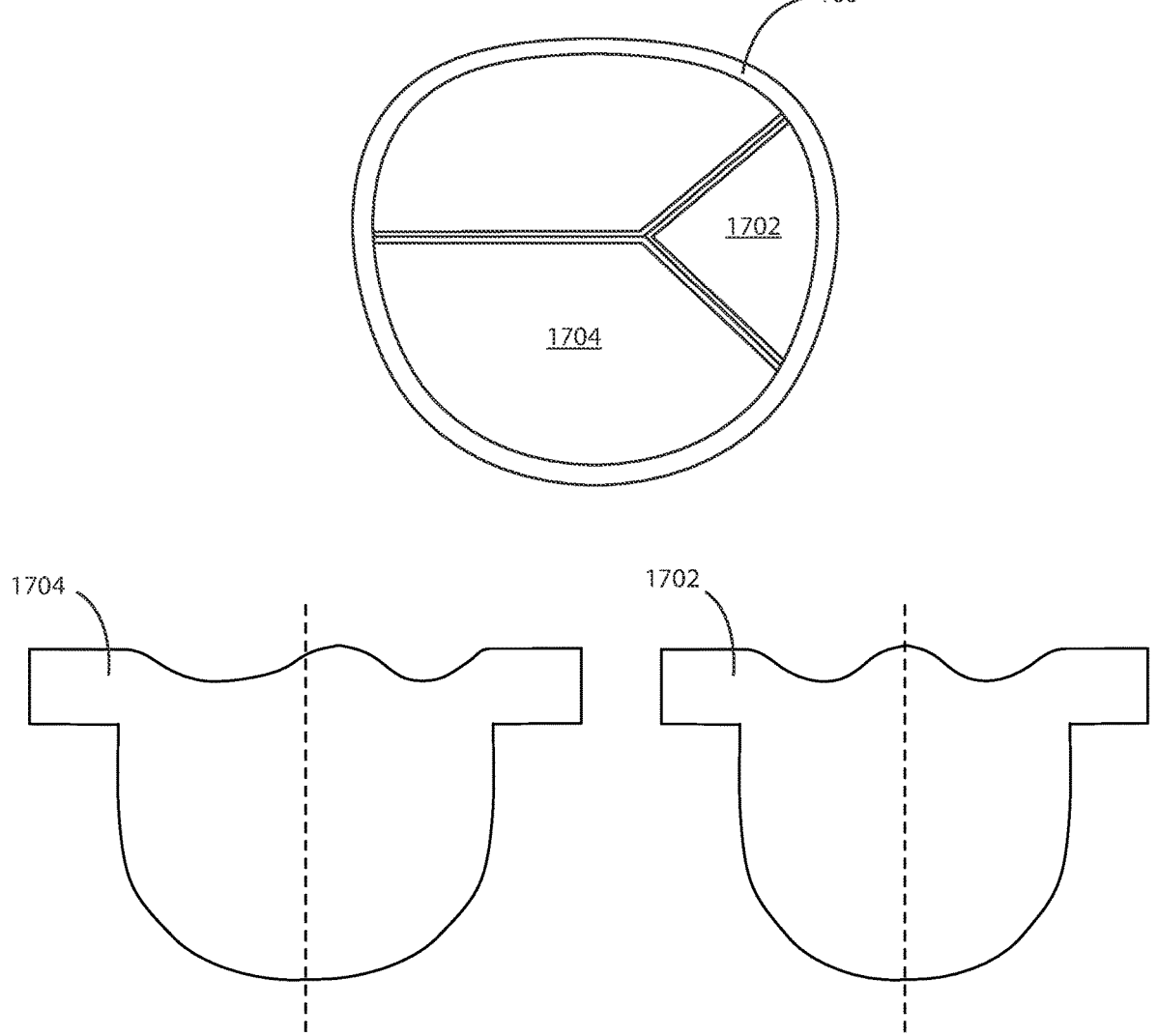
FIG. 17 is a schematic end view of a close valve with a non-circular frame and a separate view of two valve leaflets disposed therein according to various embodiments herein.

In the embodiment of FIG. 16, the central point where the three valve leaflets meet is laterally centered (wherein the flat portion of the "D" shape defines the lateral axis in this example). However, in other embodiments, the central point where the three valve leaflets meet may not be laterally centered. Referring now to FIG. 17, a schematic end view of a closed valve 100 with a non-circular frame is shown along with a view of two valve leaflets that would be disposed within the valve frame according to various embodiments herein. In this example, a first valve leaflet 1702 can have a centered peak, while a second valve leaflet 1704 can have a peak that is offset to one side (wherein the lateral center of each valve leaflet is indicated by the dashed line). In this example, the central point where the three valve leaflets meet is laterally offset to the right (in this view) but could also be offset to the left. The lateral offset can be 0.5, 1, 2, 3, 4, 5, 6, 7, 8, 9, 10, 12, 13, 14, 15, 16, 17, 18, 19, or 20 mm to the right or left, or within a range between any of the foregoing. In some embodiments, the central point where the three valve leaflets meet could also be vertically offset up or down. The vertical offset can be 0.5, 1, 2, 3, 4, 5, 6, 7, 8, 9, 10, 12, 13, 14, 15, 16, 17, 18, 19, or 20 mm up or down, or within a range between any of the foregoing.

Figure 18:
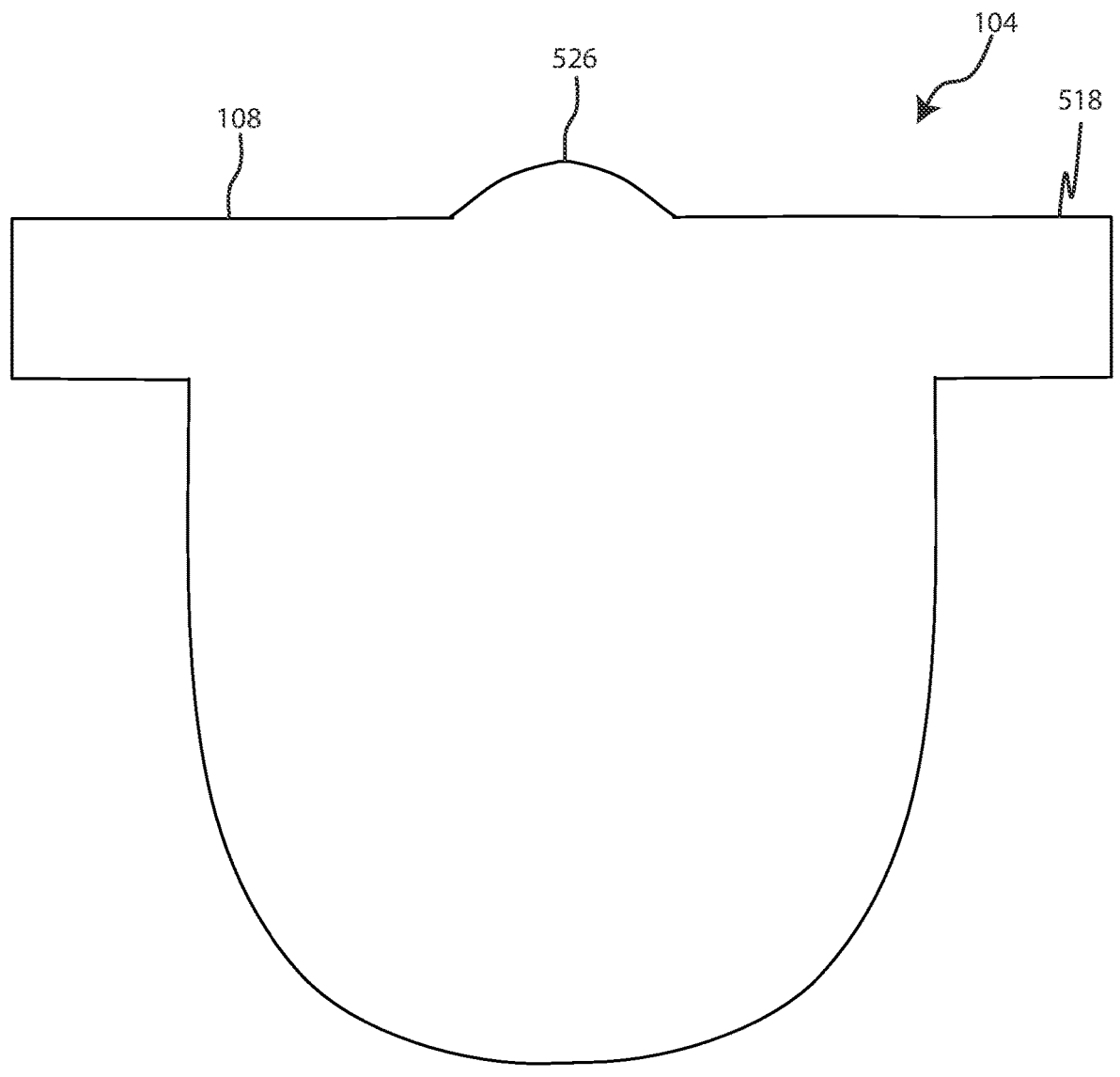
FIG. 18 is a schematic front view of a prosthetic valve leaflet, according to various embodiment.

In some embodiments, the leaflet 104 can include a central peak 526 without any valleys 528, such as shown in FIG. 18. The free edge 108 can include a planar or flat coaptation edge, such as an edge that is consistent with the top edge of the mounting tab 518, with the exception of the central peak 526. The central peak 526 can be a portion of the coaptation edge, such that the central peak 526 does not extend from one mounting tab 518 to the other mounting tab 518. At least a portion of the coaptation edge can include a planar portion located on one or both sides of the central peak 526. The central peak 526 can have a width at its ½ height that is less than half of the width of the leaflet 104 or the distance between the mounting tabs 518. In some embodiments, the central peak 526 can have a width at its ½ height that is at least about 1% and not more than about 20% of the width of the leaflet or the distance between the mounting tabs 518.

Materials

The valve disclosed herein can be made of various materials including synthetic materials and animal tissues. In some embodiments, at least a portion of the valve, for example, the leaflets or a portion of the tubular body, can be made of various synthetic materials. In some embodiments, the valve can be entirely made of synthetic materials. Synthetic leaflets must be designed to withstand repetitive stresses over a substantial length of time. The synthetic materials of the valve can include polymeric materials, metals, ceramics, and combinations thereof. In some cases, synthetic materials of the valve can include a composite material composed of at least two constituent materials with different physical and/or chemical properties. By incorporating different materials with different properties into a leaflet composite material, the physical, chemical and/or mechanical properties of the composite material can be tailored, as desired.

In some cases, the leaflets can be made (entirely or partially) from tissue obtained from an animal, e.g., a pig or a cow. In some cases, for example, a portion of the leaflets can be made from bovine pericardium or porcine tissue, such as porcine native leaflets and porcine pericardium.

Dimensions/Ratios

Figure 19:
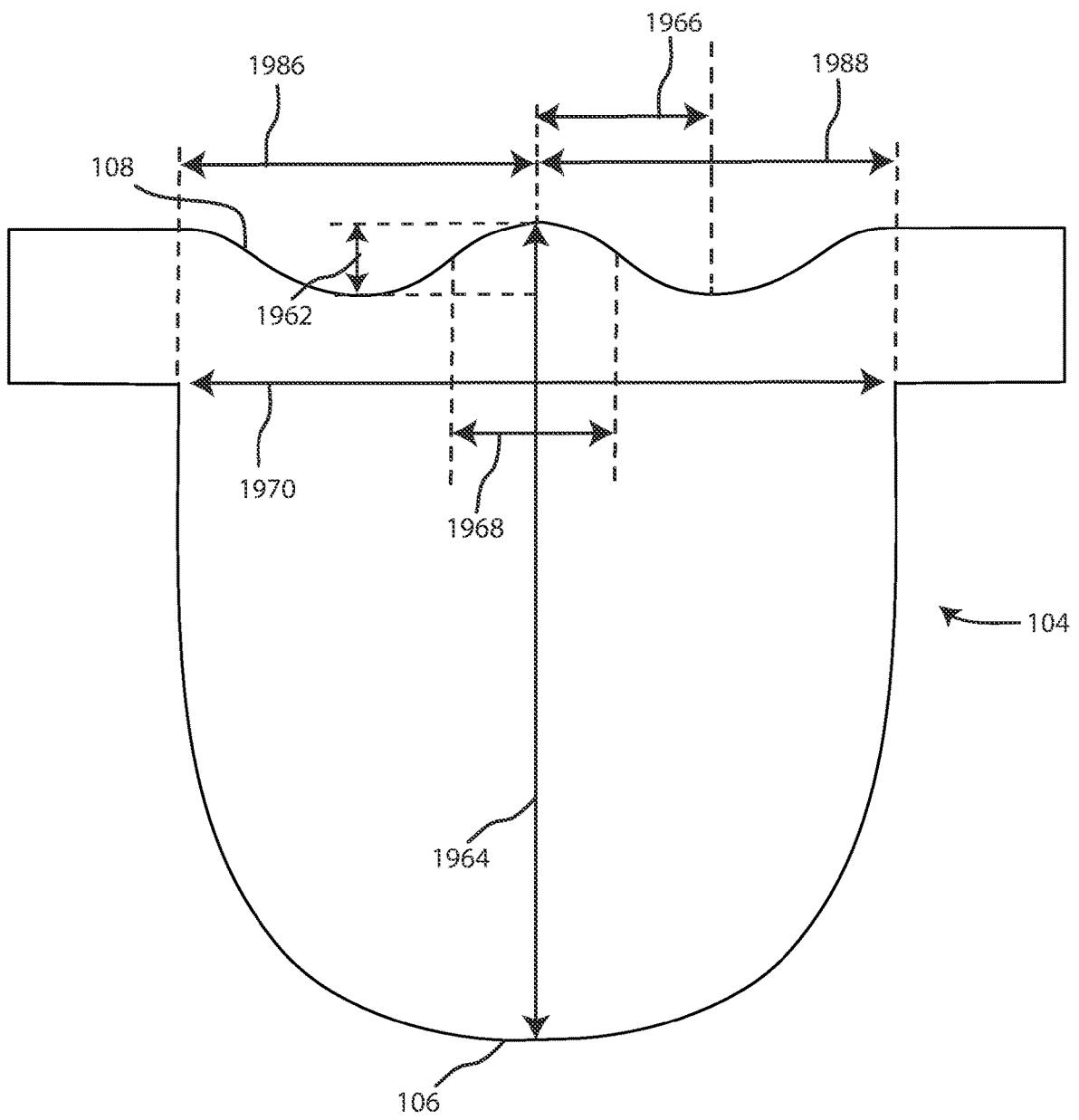
FIG. 19 is a schematic front view of a prosthetic valve leaflet, according to various embodiments.

FIG. 19 shows a front view of a leaflet 104, according to various embodiments. In various embodiments, the distance 1962 between the central peak 526 and the valleys 528 along an axis extending from the free edge 108 to the root edge 106 is approximately 0.5 mm, 1.0 mm, 1.5 mm, 2.0 mm, 2.5 mm, 3.0 mm, 3.5 mm, 4 mm, 4.5 mm, 5.0 mm. In some embodiments, the distance 1962 falls within a range wherein any of the foregoing distances can serve as the upper or lower bound of the range.

In various embodiments, the distance 1962 is approximately 5 to 20 percent of the overall height 1964 of the leaflet body on an axis extending from the free edge 108 to the root edge 106. In various embodiments, the distance 1962 is approximately 10 to 15 percent of the overall height 1964 of the leaflet body 516 on an axis extending from the free edge 108 to the root edge 106.

In some embodiments, the overall height 1964 can be about 16 mm, 17 mm, 18 mm, 19 mm, 20 mm, 21 mm, 22 mm, 23 mm or 24 mm. In some embodiments, the overall height 1964 can fall within a range wherein any of the foregoing heights can serve as the upper or lower bound of the range.

In some embodiments, the distance 1966 between the apex of the central peak 526 and the bottom of each adjoining valley 528 along an axis perpendicular to the axis extending from the free edge 108 to the root edge 106 can be about 4 mm, 5 mm, 6 mm, 7 mm, 8 mm, or 9 mm. In some embodiments, the distance 1966 can fall within a range wherein any of the foregoing distances can serve as the upper or lower bound of the range.

In some embodiments, the width 1968 of the central peak 526 at ½ height is at least 10 percent and not more than 20 percent of the overall width 1970 of the leaflet body 516 excluding any commissural mounting tabs. The width of the central peak 526 at ½ height can refer to the width of the central peak 526 as measured between two points along the profile that fall at a point that is exactly half the height of the maximum height of the central peak 526 as measured from the bottom of the adjoining valleys.

In some embodiments, the width 1970 of the leaflet body 516 excluding any commissural mounting tabs 518 is about 20 mm, 22 mm, 24 mm, 26 mm, 28 mm or 30 mm. In some embodiments, the width 1970 can fall within a range wherein any of the foregoing widths can serve as the upper or lower bound of the range.

In some embodiments of asymmetrical leaflets, such as where the central peak is offset from the center line, the distance 1986 can be greater than half of the width 1970 and the distance 1988 can be less than half of the width 1970. In other embodiments of asymmetrical leaflets, the distance 1988 can be greater than half of the width 1970 and the distance 1986 can be less than half of the width 1970.

Methods

Figure 20:
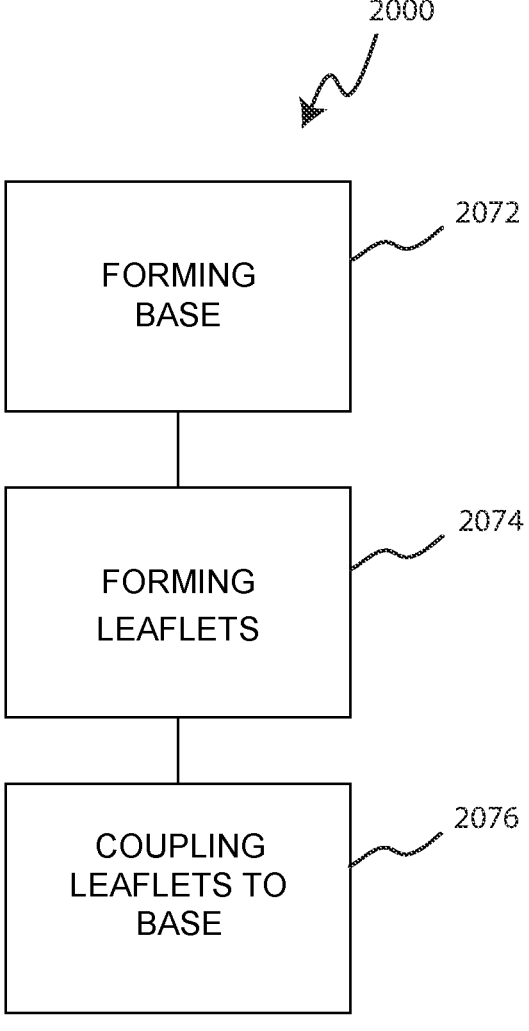
FIG. 20 is a flow chart of a method of making a prosthetic valve leaflet, according to various embodiments.

FIG. 20 shows a flow chart of a method 2000 of forming a prosthetic valve leaflet, according to various embodiments. The method 2000 can include forming a base 2072. The base can define a substantially cylindrical passage there through. The method 2000 can include forming a plurality of leaflets 2074. Each leaflet can include a free edge and a root edge. The free edge can include at least two valleys and a central peak. The central peak can be disposed between the two valleys. The method 2000 can further include coupling the root edge of each leaflet to the base 2076, such that each free edge is substantially opposite from the root edge and moveable relative to the root edge to coapt with a respective edge portion of at least one of the other leaflets.

Figure 21:
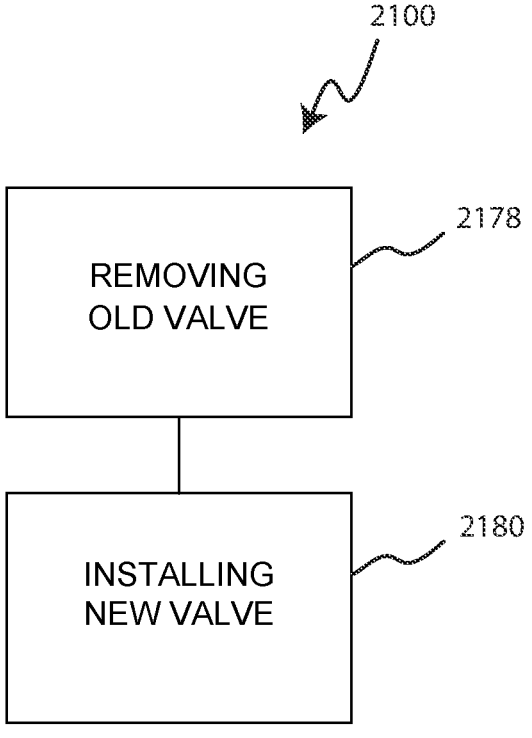
FIG. 21 is a flow chart of a method of replacing a prosthetic valve leaflet, according to various embodiments.

FIG. 21 shows a flow chart of a method 2100 of replacing a prosthetic valve leaflet, according to various embodiments. The method 2100 can include removing an old valve 2178. The old valve can be a prosthetic valve that has deteriorated or otherwise failed. In other embodiments, the old valve can be the original natural valve that has failed.

The method 2100 can include installing a new valve in place of the old valve 2180. The new valve can include a plurality of leaflets coupled to a base. Each of the leaflets can include a root edge coupled to the base and a free edge configured to coapt with the respective edge portion of at least one of the other leaflets. The free edge can include at least two valleys and a central peak. The central peak can be disposed between the two valleys.

It will be appreciated, however, that in some embodiments the old valve may not be removed. Instead, the new valve may simply be positioned within the old valve and then deployed into place effectively disposed within the perimeter of the old valve.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A valve leaflet for an implantable valve device comprising:
   a leaflet body comprising:
      a free edge configured for coaptation with free edges of one or more other valve leaflets, the free edge comprising an edge profile comprising
         a peak; and
         valleys disposed on opposite sides of the peak;
      a root edge disposed opposite the free edge; and
      commissural mounting tabs disposed on opposed lateral sides of the leaflet body;
   wherein a top of the peak falls below a top of the commissural mounting tabs;
   wherein the free edge connects with a superior portion of each of the commissural mounting tabs, such that the valleys are located inferiorly to the connections of the free edge with the commissural mounting tabs.

2. The valve leaflet of claim 1, wherein a thickness of the leaflet body is greater at the peak than at the valleys.

3. The valve leaflet of claim 1, wherein a thickness of the leaflet body at the peak is from 0.3 to 0.4 mm and at the valleys is from 0.2 to 0.3 mm.

4. The valve leaflet of claim 1, wherein a distance between the peak and the valleys along an axis extending from the free edge to the root edge is approximately 0.5 mm to 4 mm.

5. The valve leaflet of claim 1, wherein a distance between the peak and the valleys along an axis extending from the free edge to the root edge is approximately 1 mm to 3 mm.

6. The valve leaflet of claim 1, wherein a distance between the peak and the valleys along an axis extending from the free edge to the root edge is approximately 5 to 20 percent of an overall height of the leaflet body along the same axis.

7. The valve leaflet of claim 1, wherein a distance between the peak and the valleys along an axis extending from the free edge to the root edge is approximately 10 to 15 percent of an overall height of the leaflet body along the same axis.

8. The valve leaflet of claim 1, wherein a distance between the peak and each adjoining valley along an axis perpendicular to the axis extending from the free edge to the root edge is from 4 mm to 9 mm.

9. The valve leaflet of claim 1, wherein a width of the peak at ½ height is from 10 to 20 percent of an overall width of the leaflet body excluding the commissural mounting tabs.

10. The valve leaflet of claim 1, wherein a width of the leaflet body excluding the commissural mounting tabs is from 20 to 30 mm.

11. The valve leaflet of claim 1, the peak comprising a notch.

12. The valve leaflet of claim 1, wherein the peak is centered along a width of the leaflet body.

13. The valve leaflet of claim 1, wherein the free edge has at least two inflection points;
   wherein the peak is disposed between the two inflection points.

14. The valve leaflet of claim 1, wherein the commissural mounting tabs are planar with at least a portion of the leaflet body that defines the free edge and a portion of the leaflet body that defines the root edge.

15. A valve leaflet for an implantable valve device comprising:
   a leaflet body comprising:
      a free edge configured for coaptation with free edges of one or more other valve leaflets, the free edge comprising an edge profile comprising
         a peak; and
         valleys disposed on opposite sides of the peak;
      a root edge disposed opposite the free edge; and
      commissural mounting tabs disposed on opposed lateral sides of the leaflet body;
   wherein a top of the peak falls below a top of the commissural mounting tabs;
   wherein the free edge extends between the commissural mounting tabs;
   wherein a superior axis is defined between the two points at which the free edge connects with the commissural mounting tabs;
   wherein at least a portion of the free edge extends inferiorly to the superior axis.

16. The valve leaflet of claim 15, wherein a thickness of the leaflet body is greater at the peak than at the valleys.

17. The valve leaflet of claim 15, wherein a thickness of the leaflet body at the peak is from 0.3 to 0.4 mm and at the valleys is from 0.2 to 0.3 mm.

* * * * *